(12) United States Patent
Luo et al.

(10) Patent No.: US 11,319,339 B2
(45) Date of Patent: May 3, 2022

(54) MULTI-CHANNEL PEPTIDE SYNTHESIZER AND OPERATING METHOD THEREOF

(71) Applicant: HUNAN UNIVERSITY OF SCIENCE AND ENGINEERING, Hunan (CN)

(72) Inventors: Xiaofang Luo, Hunan (CN); Yulu Gong, Hunan (CN); Zuodong Qin, Hunan (CN); Zongcheng Wang, Hunan (CN); Pingkai Ouyang, Hunan (CN)

(73) Assignee: HUNAN UNIVERSITY OF SCIENCE AND ENGINEERING, Yongzhou (CN)

( * ) Notice: Subject to any disclaimer, the term of this patent is extended or adjusted under 35 U.S.C. 154(b) by 460 days.

(21) Appl. No.: 16/439,538

(22) Filed: Jun. 12, 2019

(65) Prior Publication Data
US 2020/0048302 A1 Feb. 13, 2020

(30) Foreign Application Priority Data

Aug. 8, 2018 (CN) .......................... 201810896961.3

(51) Int. Cl.
*B01J 19/00* (2006.01)
*C07K 1/04* (2006.01)
*C07K 1/14* (2006.01)

(52) U.S. Cl.
CPC ........... *C07K 1/045* (2013.01); *B01J 19/0046* (2013.01); *B01J 2219/00286* (2013.01); *B01J 2219/00725* (2013.01)

(58) Field of Classification Search
CPC .... B01J 19/00; B01J 19/0046; B01J 2219/00;
B01J 2219/00274; B01J 2219/00277;
B01J 2219/00279; B01J 2219/00281;
B01J 2219/00286; B01J 2219/00306;
B01J 2219/00324; B01J 2219/00326;
(Continued)

(56) References Cited

U.S. PATENT DOCUMENTS

| | | | |
|---|---|---|---|
| 8,003,370 B2 * | 8/2011 | Maltezos | B01L 7/52 435/283.1 |
| 2010/0311946 A1 * | 12/2010 | Srivastava | C07K 7/23 530/328 |
| 2015/0118715 A1 * | 4/2015 | Wittwer | B01L 7/5255 435/91.2 |

FOREIGN PATENT DOCUMENTS

| CN | 107056879 A | 8/2017 |
|---|---|---|
| CN | 207153616 U | 3/2018 |

(Continued)

*Primary Examiner* — Natasha E Young

(57) ABSTRACT

Disclosed is a multi-channel peptide synthesizer, including a gas-bath thermotank, a plurality of reactor tubes, a motor, a rotating rack, a liquid-feeding tube, a feeding device, a vacuum tube and a nitrogen tube. The gas-bath thermotank body provides a desired constant temperature for reaction. The reactor tube provides a place for peptide synthesis and resin washing. The motor and the rotating rack are used to fully mix the reaction and cleaning solutions. Various liquid reagents required are fed to the reactor tube through the liquid-adding tube. Various materials required are prepared in advance in the feeding device and directly fed to the reactor tube. The reaction or washing solution in the reactor tube is pumped to a waste liquid tank through the vacuum tube. Nitrogen is introduced into each reactor tube through the nitrogen tube. This device can be applied in batch-wise peptide synthesis using solid-phase methods.

12 Claims, 4 Drawing Sheets

(58) Field of Classification Search
CPC .... B01J 2219/00331; B01J 2219/00333; B01J 2219/00337; B01J 2219/00342; B01J 2219/00351; B01J 2219/00389; B01J 2219/00414; B01J 2219/00418; B01J 2219/00423; B01J 2219/00479; B01J 2219/00488; B01J 2219/00583; B01J 2219/00585; B01J 2219/00596; B01J 2219/00603; B01J 2219/00657; B01J 2219/00718; B01J 2219/0072; B01J 2219/00725; C07K 1/00; C07K 1/04; C07K 1/045; C07K 1/06; C07K 1/14
See application file for complete search history.

(56) References Cited

FOREIGN PATENT DOCUMENTS

| | | | |
|---|---|---|---|
| CN | 208776625 U | 4/2019 | |
| WO | WO-2008138337 A2 * | 11/2008 | .......... B01J 19/0046 |

* cited by examiner

MULTI-CHANNEL PEPTIDE SYNTHESIZER AND OPERATING METHOD THEREOF

CROSS REFERENCE TO RELATED APPLICATIONS

This application claims the benefit of priority from Chinese Patent Application No. 201810896961.3, filed on Aug. 8, 2018. The content of the aforementioned application, including any intervening amendments thereto, is incorporated herein with reference in its entirety.

TECHNICAL FIELD

The application relates to peptide synthesizers, particularly to a multi-channel peptide synthesizer, and more particularly to batch-wise peptide synthesis using a solid-phase method.

BACKGROUND

In the past one hundred years, research on peptide synthesis has made great progress, and initially focused on peptide synthesis using liquid-phase method. In 1963, Merrifield first proposed solid-phase peptide synthesis (SPPS); and in 1972, Lou Carpino improved the SPPS. With the continuous development of the synthetic techniques for peptides, more and more active peptides are synthesized and widely applied in drug, food, beverage, daily chemical products, animal husbandry, and so on.

Currently, the most widely used solid-phase peptide synthesis method is Fmoc SSPS in which the first amino acid of a target peptide is loaded onto the solid phase carrier; the amino-protecting group is removed; the second amino acid of the target peptide is condensed with the first amino acid; and deprotection-washing-condensation-washing is repeated until the last amino acid of the target peptide is condensed with the peptide on the carrier. The target peptide is then cleaved from the solid phase carrier to obtain a crude product which is further purified and lyophilized to obtain a pure target peptide.

There are many defects in the existing multi-channel peptide synthesizers, for example, insufficient channels, complex operation, uncontrollable temperature, difficulty in regulating nitrogen blowing, and low feeding efficiency, leading to low synthesis efficiency and making it difficult to meet the requirements of the current peptide screening and peptide library construction. The existing solid-phase peptide synthesizers are generally simply manufactured and provided with a small number of channels. In these synthesizers, the resin and the solution are mixed uniformly by nitrogen blowing. However, such synthesizers generally fail to provide controllable temperature, which is very unfavorable to the reaction, especially in the winter; the number of channels is only about 10; the liquid reagent is extruded into the reactor by a wash bottle; and the nitrogen valve needs to be repeatedly opened and closed for each washing and reaction and it is also required that the nitrogen introduced to each reactor is adjusted at any time. In the feeding, the required amino acids are usually needed to be weighed to the weighing papers in advance and then added to the reactor one by one. When the reaction is conducted under nitrogen blowing, the nitrogen in a small amount may fail to cause complete swelling of the resin while in a larger amount may make it easy to blow the resin to the wall of the reactor, resulting in incomplete reaction of the partial resin.

SUMMARY

The application provides an operable, efficient and stable multi-channel peptide synthesizer and an operating method thereof to overcome the defects and shortcomings in the prior art.

An object of the application is to provide a multi-channel peptide synthesizer, comprising: a gas bath-heating thermotank; and a storage and feeding device; wherein a rotating shaft is provided in the gas bath-heating thermotank; a plurality of reactor tubes are fixed to the rotating shaft; one end of each reactor tube is connected to a solvent-delivering tube through which respective openings at the end of respective reactor tubes are connected in series; the other end of each reactor tube is connected to a pressure hose through which respective openings at the other end of respective reactor tubes are connected in series; a communicating end of the solvent-delivering tube is provided with a first multi-way valve for supplying liquid; a communicating end of the pressure hose is provided with a second multi-way valve for vacuuming or nitrogen blowing; the rotating shaft is driven by an adjustable-speed motor to rotate to drive the reactor tubes to flip vertically; and the storage and feeding device is configured to store materials and feed materials to the reactor tubes.

In an embodiment, the solvent-delivering tube extends into the rotating shaft at one end of the rotating shaft and extends along an axis of the rotating shaft to an outside of the gas bath-heating thermotank; the pressure hose extends into the rotating shaft at the other end of the rotating shaft and extends along the axis of the rotating shaft to the outside of the gas bath-heating thermotank; and the reactor tubes rotate to drive the solvent-delivering tube and the pressure hose respectively at two ends of the reactor tubes to rotate.

In an embodiment, a lead valve is provided at a channel port at which the first multi-way valve is connected with the solvent-delivering tube and at a channel port at which the second multi-way valve is connected with the pressure hose, respectively.

In an embodiment, the first multi-way valve at the communicating end of the solvent-delivering tube is a four-way valve provided with four channel ports, wherein three of the four channel ports of the four-way valve are respectively a methanol inlet, a deprotection solvent inlet and a methylformamide inlet, and another channel port is connected with the solvent-delivering tube and a lead valve of the four-way valve is provided where the another channel port is.

In an embodiment, the second multi-way valve at the communicating end of the pressure hose is a three-way valve provided with three channel ports, wherein two of the three channel ports of the three-way valve are respectively a nitrogen connection port and a vacuum connection port, and another channel port is connected with the pressure hose and a lead valve of the three-way valve is provided where the another channel port is; and the nitrogen connection port is connected to a nitrogen pressure cylinder and the vacuum connection port is connected to a vacuum pump.

In an embodiment, each reactor tube comprises a cover, a straight tube and a bottom tube which connect to each other; and a top of the cover and a bottom of the bottom tube are respectively provided with a hose connection port, and a top valve and a bottom valve are respectively provided at the hose connection ports.

In an embodiment, the cover is a rubber seal cover which is detachably connected with the straight tube; and the straight tube is in threaded connection with the bottom tube.

In an embodiment, the storage and feeding device comprises a material storage tank and a solvent conduit; one end of the solvent conduit extends into the material storage tank, and the other end of the solvent conduit serves as a discharge port configured to feed materials to the reactor tubes and provided with a feeding valve; and a part of the solvent conduit is coiled in a stretchable hose device.

In an embodiment, the reactor tubes are arranged in two rows and respectively fixed to two sides of the rotating shaft; the rotating shaft is horizontally arranged with both ends mounted on a tank body of the gas bath-heating thermotank by a rotatable seal joint; the rotating shaft is further provided with a vertical solid support for fixing the pressure hose and the solvent-delivering tube; and the tank body of the gas bath-heating thermotank is provided with a vent fan for adjusting temperature and keeping the temperature constant in the tank body.

Another aspect of the invention further provides a method of operating a multi-channel peptide synthesizer, comprising:

1) Swelling of Resin setting a reaction temperature; turning on a heating switch of the tank body of the gas bath-heating thermotank; placing a resin in the reactor tube of a channel and closing the unused channels; covering the reactor tube by the cover; closing a door of the tank body of the gas bath-heating thermotank; closing the lead valve of the three-way valve and regulating the four-way valve for communication with the methylformamide inlet; opening the lead valve of the four-way valve to allow the addition of methylformamide to the reactor tube of the channel; closing the lead valve of the four-way valve; and turning on and controlling the adjustable-speed motor to an appropriate rotation speed to swell the resin;

2) Deprotection of Resin turning off the adjustable-speed motor to keep the reactor tubes in a vertical form; regulating the three-way valve for communication with the vacuum connection port; opening the lead valve of the three-way valve to allow the methylformamide in the reactor tubes of individual channels to be pumped; closing the lead valve of the three-way valve and regulating the four-way valve for communication with the deprotection solvent inlet; opening the lead valve of the four-way valve to allow the adding of the deprotection solvent to the reactor tubes of individual channels; closing the lead valve of the four-way valve; and turning on and controlling the adjustable-speed motor to an appropriate rotation speed to start the deprotection;

3) Washing of Resin and Feeding for Reaction turning off the adjustable-speed motor to keep the reactor tubes in a vertical form; regulating the three-way valve for communication with the vacuum connection port; opening the lead valve of the three-way valve to allow the liquid in the reactor tubes of individual channels to be pumped; closing the lead valve of the three-way valve and regulating the four-way valve for communication with the methylformamide inlet; opening the lead valve of the four-way valve to allow the addition of methylformamide to the reactor tubes of individual channels; closing the lead valve of the four-way valve; turning on and controlling the adjustable-speed motor to an appropriate rotation speed to start the washing; repeating the above process to wash the resin five times; opening a top cover of the tank body of the gas bath-heating thermotank; opening the cover and selecting the materials in their corresponding material storage tanks and adding the materials sequentially to the reactor tubes of individual channels; covering the reactor tube by the cover and closing the top cover of tank body of the gas bath-heating thermotank; turning on and controlling the adjustable-speed motor to an appropriate speed to start the condensation of amino acids;

4) Washing after Reaction turning off the adjustable-speed motor to keep the reactor tubes in a vertical form; regulating the three-way valve for communication with the vacuum connection port; opening the lead valve of the three-way valve to allow the liquid in the reactor tubes of individual channels to be pumped; closing the lead valve of the three-way valve and regulating the four-way valve for communication with the methylformamide inlet; opening the lead valve of the four-way valve to allow the addition of methylformamide to the reactor tubes of individual channels; closing the lead valve of the four-way valve; turning on and controlling the adjustable-speed motor to an appropriate speed to start the washing; repeating the above process to wash the resin three times; and repeating steps 2-4 until the condensation of all desired amino acids is completed; and 5) Washing and Drying of Resin turning off the adjustable-speed motor to keep the reactor tubes in a vertical form; regulating the three-way valve for communication with the vacuum connection port; opening the lead valve of the three-way valve to allow the liquid in the reactor tubes of individual channels to be pumped; closing the lead valve of the three-way valve and regulating the four-way valve for communication with the methanol inlet; opening the lead valve of the four-way valve to allow the adding of methanol to the reactor tubes of individual channels; closing the lead valve of the four-way valve; turning on and controlling the adjustable-speed motor to an appropriate speed to start the washing; repeating the above process to wash the resin three times; regulating the three-way valve for communication with the vacuum connection port; opening the lead valve of the three-way valve and maintaining the vacuuming until the resin is completely dried; and collecting the peptide resin.

The application has the following beneficial effects.

The application provides multiple channels for simultaneous reaction and involves simple operation, high efficiency and stability. For the existing peptide synthesizers, one person can generally only perform about 10 reactions, and liquid reagents are squeezed into the reactor by washing bottles. In addition, the nitrogen valve needs to be repeatedly opened and closed for each washing and reaction and the nitrogen amount also needs to be adjusted at any time. Moreover, the feeding is also inconvenient. A novel multi-channel peptide synthesizer disclosed by the invention is provided with a gas bath-heating thermotank body, double-row multi-channel reactor tubes, a rotating shaft, an adjustable-speed motor, a feeding device, a liquid-adding tube, a vacuum tube and a nitrogen tube. The reactor tubes are provided on the rotating shaft and are driven by the adjustable-speed motor to uniformly mix the materials. The materials are stored in advance in the material storage tank so that the materials can be directly fed to the reactor tubes when the feeding is required. This device is kept in the gas bath-heating thermotank body to allow for a constant reaction temperature.

The multi-channel peptide synthesizer of the invention can simultaneously synthesize 1-48 peptides. In the case where a small number of peptides are synthesized simultaneously, the reaction mixture can be mixed by nitrogen blowing; and when a large number of peptides are required to be synthesized simultaneously, the reaction mixture can be mixed by the adjustable-speed motor.

When using the multi-channel peptide synthesizer of the invention to synthesize peptides, the number of reactions can be reduced or increased at any time by closing or opening the top valve or the bottom valve. The synthesis reaction which is completed can be removed and new reaction can also be conducted at any time. The reaction of individual channels is conducted independently without affecting each other. Therefore, the device of the invention involves continuous multi-channel production capacity, greatly improving the efficiency in the massive synthesis of customized peptides, the screening of peptide with an antibody and the construction of peptide libraries.

Other aspects and advantages of the invention will be set forth below, and some of them will become clear with reference to the following description or the embodiments of the invention.

Figure 1:
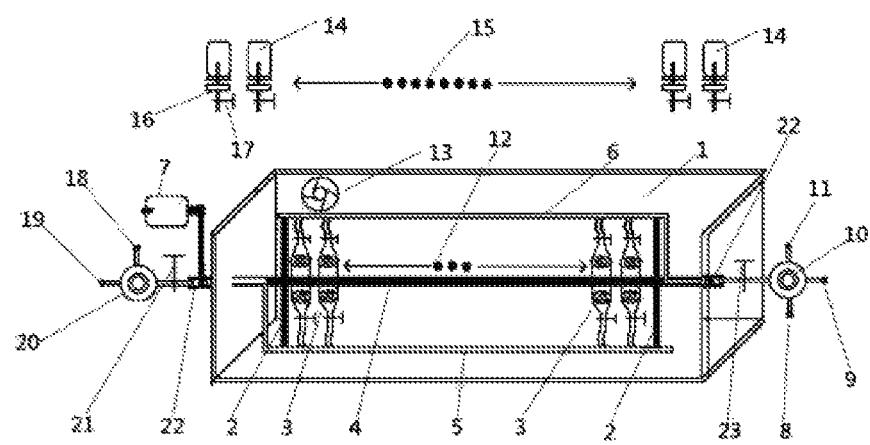
FIG. 1 schematically shows a multi-channel peptide synthesizer of the invention.

In the drawings: 1—gas bath-heating thermotank; 2—solid support; 3—reactor tube; 4—rotating shaft; 5—pressure hose; 6—solvent-delivering tube; 7—adjustable-speed motor; 8—methanol inlet; 9—deprotecting solvent inlet; 10—four-way valve; 11—methylformamide inlet; 12—omitted reactor tubes; 13—vent fan; 14—material storage tank; 15—omitted material storage tanks; 16—stretchable hose device; 17—feeding valve; 18—nitrogen connection port; 19—vacuum connection port; 20—three-way valve; 21—lead valve of the three-way valve; 22—rotatable seal joint; 23—lead valve of the four-way valve; 24—cover; 25—straight tube; 26—thread port of the straight tube; 27—seal ring; 28—sand core chip; 29—thread pot of the bottom tube; 30—mesh sieve of the bottom tube; 31—bottom valve; 32—hose connection port; 33—top valve; and 34—solvent conduit.

DETAILED DESCRIPTION OF EMBODIMENTS

The invention will be described in detail below with reference to the drawings and embodiments.

Example 1

Figure 2:
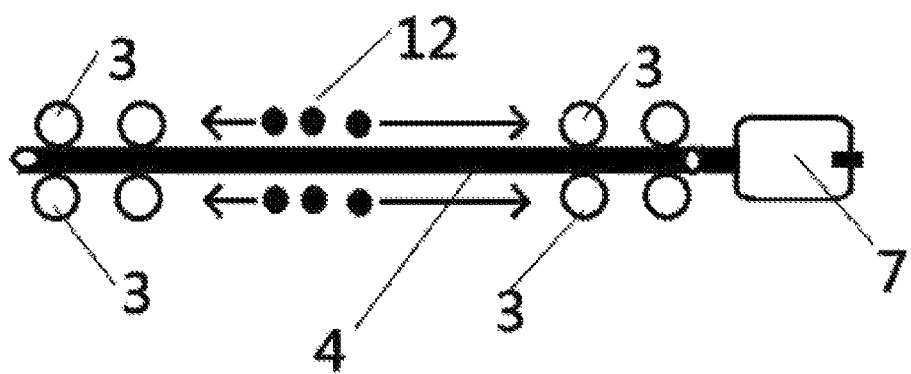
FIG. 2 schematically shows the arrangement of reactor tubes at both sides of a rotating shaft in the multi-channel peptide synthesizer of the invention.
Figure 3:
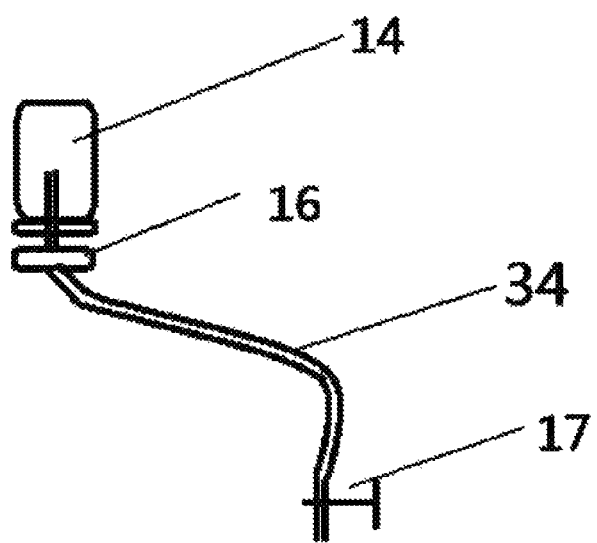
FIG. 3 schematically shows a material storage tank of the multi-channel peptide synthesizer of the invention.
Figure 4:
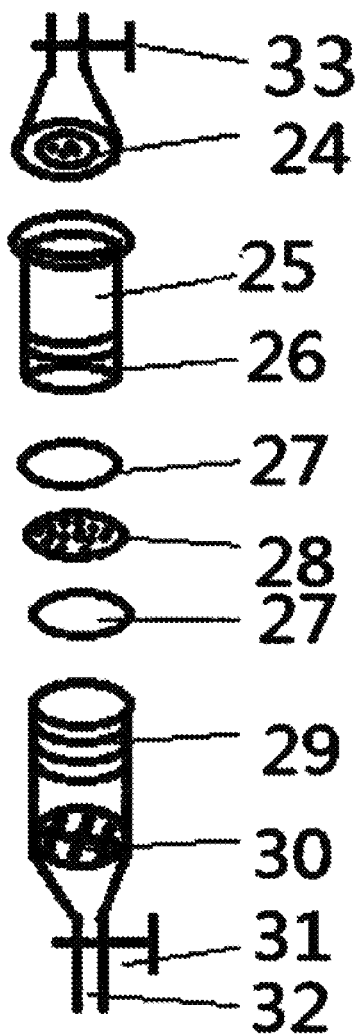
FIG. 4 schematically shows the reactor tube of the multi-channel peptide synthesizer of the invention.

As shown in FIGS. 1-4, a multi-channel peptide synthesizer includes a gas bath-heating thermotank 1 and a storage and feeding device. A rotating shaft 4 is provided in the gas bath-heating thermotank 1 and a plurality of reactor tubes 3 are fixed to the rotating shaft 4. One end of the reactor tube 3 is connected to a solvent-delivering tube 6 through which respective openings at the end of respective reactor tubes are connected in series. The other end of the reactor tube is connected to a pressure hose 5 through which respective openings at the other end of respective reactor tubes are connected in series. A communicating end of the solvent-delivering tube 6 is provided with a first multi-way valve for supplying liquid. A communicating end of the pressure hose 5 is provided with a second multi-way valve for vacuuming or nitrogen blowing. The rotating shaft 4 is driven by an adjustable-speed motor 7 to rotate to drive the reactor tubes to flip vertically. The storage and feeding device is used to store materials and feed materials to the reactor tubes.

In this embodiment, the solvent-delivering tube 6 extends into the rotating shaft 4 at one end of the rotating shaft 4 and extends along an axis of the rotating shaft 4 to an outside of the gas bath-heating thermotank 1. The pressure hose 5 extends into the rotating shaft 4 at the other end of the rotating shaft 4 and extends along the axis of the rotating shaft 4 to the outside of the gas bath-heating thermotank 1. The reactor tubes rotate to drive the solvent-delivering tube 6 and the pressure hose 5 respectively provided at two ends of the reactor tubes 3 to rotate.

In this embodiment, the first multi-way valve at the communicating end of the solvent-delivering tube 6 is a four-way valve provided with four channel ports, of which three are respectively a methanol inlet, a deprotection solvent inlet and a methylformamide inlet, and another channel port is connected with the solvent-delivering tube 6 and a lead valve 23 of the four-way valve is provided at the another channel port. The second multi-way valve at the communicating end of the pressure hose 5 is a three-way valve 20 provided with three channel ports, of which two are respectively a nitrogen connection port 18 and a vacuum connection port 19, and another channel port is connected with the pressure hose 5 and a lead valve of the three-way valve is provided at the another channel port. The nitrogen connection port 18 is connected to a nitrogen pressure cylinder and the vacuum connection port 19 is connected to a vacuum pump.

In an embodiment, the reactor tube 3 includes a cover 24, a straight tube 25 and a bottom tube which connect to each other. A top of the cover 24 and a bottom of the bottom tube are respectively provided with a hose connection port 32, and a top valve 33 and a bottom valve 31 are respectively provided at the two hose connection ports 32. The cover 24 is a rubber seal cover, which is detachably connected with the straight tube 25. The straight tube 25 is in threaded connection with the bottom tube.

In this embodiment, the storage and feeding device includes a material storage tank 14 and a solvent conduit 34. One end of the solvent conduit 34 extends into the material storage tank 14, and the other end of the solvent conduit 34 serves as a discharge port configured to feed materials to the reactor tubes 3 and is provided with a feeding valve. A part of the solvent conduit 34 is coiled in a stretchable hose device 16. The solvent conduit 34 can be pulled out from the stretchable hose device 16 and can be automatically retracted by the stretchable hose device 16.

In this embodiment, the reactor tubes 3 are arranged in two rows and respectively fixed to two sides of the rotating shaft 4. The rotating shaft 4 is horizontally arranged with both ends mounted on a body of the gas bath-heating thermotank 1 by a rotatable seal joint 22. The rotating shaft 4 is further provided with a vertical solid support 2 for fixing the pressure hose 5 and the solvent-delivering tube 6. The body of the gas bath-heating thermotank 1 is provided with a vent fan 13 for adjusting temperature and keeping the temperature constant in the tank body.

Example 2

The multi-channel peptide synthesizer in Example 1 was employed to synthesize the same peptide sequence using the reactor tubes of 48 channels, and the peptide sequence was shown as VRVALCTAGG. The specific process was described as follows.

(1) Swelling of Resin

The reaction temperature was set to 30° C. and the gas bath-heating thermotank 1 was turned on for heating. Fmoc-Gly-Wang Resins were respectively placed in the reactor tubes 3 of individual channels and the reactor tube was covered by the cover. A door of the body of the gas bath-heating thermotank 1 was closed. The lead valve 21 of the three-way valve 20 was closed and the four-way valve 10 was regulated for communication with the methylformamide inlet 11. The lead valve 23 of the four-way valve 10 was opened to allow the addition of methylformamide to the reactor tubes 3 of individual channels. The lead valve 23 of the four-way valve 10 was closed and the adjustable-speed motor 7 was turned on and controlled to an appropriate rotation speed to swell the resin.

(2) Deprotection

The adjustable-speed motor 7 was turned off to keep the reactor tubes 3 in a vertical form. The three-way valve 20 was regulated for communication with the vacuum connection port 19. The lead valve 21 of the three-way valve 20 was opened to allow the methylformamide in the reaction tube 3 of individual channels to be pumped. Then the lead valve 21 of the three-way valve 20 was closed and the four-way valve 10 was regulated for communication with the deprotection solvent inlet 9. The lead valve 23 of the four-way valve 10 was opened to allow the adding of the deprotection solvent to the reactor tubes 3 of individual channels. The lead valve 23 of the four-way valve 10 was closed. The adjustable-speed motor 7 was turned on and controlled to an appropriate rotation speed to start the deprotection.

(3) Washing of Resin and Feeding

The adjustable-speed motor 7 was turned off to keep the reactor tubes 3 in a vertical form. The three-way valve 20 was regulated for communication with the vacuum connection port 19. The lead valve 21 of the three-way valve 20 was opened to allow the liquid in the reactor tubes 3 of individual channels to be pumped. The lead valve 21 of the three-way valve 20 was closed and the four-way valve 10 was regulated for communication with the methylformamide inlet 11. The lead valve 23 of the four-way valve 10 was opened to allow the addition of methylformamide to the reactor tubes 3 of individual channels. Then the lead valve 23 of the four-way valve 10 was closed. The adjustable-speed motor 7 was turned on and controlled to an appropriate rotation speed to start the washing. The above process was repeated to wash the resin five times. A top cover of the body of the gas bath-heating thermotank 1 was opened. The cover was opened, and the materials in material storage tanks 14 corresponding to Fmoc-Gly-OH were selected and sequentially added to the reactor tubes 3 of individual channels. The cover was covered and the top cover of the body of the gas bath-heating thermotank 1 was closed. The adjustable-speed motor was turned on and controlled to an appropriate rotation speed to start the condensation of amino acids.

(4) Washing after Reaction

The adjustable-speed motor was turned off to keep the reactor tubes 3 in a vertical form. The three-way valve 20 was regulated for communication with the vacuum connection port 19. The lead valve 21 of the three-way valve 20 was opened to allow the liquid in the reactor tubes 3 of individual channels to be pumped. The lead valve 21 of the three-way valve 20 was closed and the four-way valve was regulated for communication with the methylformamide inlet 11. The lead valve 23 of the four-way valve 10 was opened to allow the addition of methylformamide to the reactor tubes 3 of individual channels. The lead valve 23 of the four-way valve 10 was closed. The adjustable-speed motor 7 was turned on and controlled to an appropriate rotation speed to start the washing. The above process was repeated to wash the resin three times and steps 2-4 were repeated to sequentially perform condensation with Fmoc-Ala-OH, Fmoc-Thr(tBu)-OH, Fmoc-Cys(Trt)-OH, Fmoc-Leu-OH, Fmoc-Ala-OH, Fmoc-Val-OH, Fmoc-Arg(Pbf)-OH and Fmoc-Val-OH.

(5) Washing and Drying of Peptide Resin

The adjustable-speed motor 7 was turned off to keep the reactor tubes 3 in a vertical form. The three-way valve 20 was regulated for communication with the vacuum connection port 19. The lead valve 21 of the three-way valve 20 was opened to allow the liquid in the reactor tubes 3 of individual channels to be pumped. The lead valve 21 of the three-way valve 20 was closed and the four-way valve was regulated for communication with the methanol inlet 8. The lead valve 23 of the four-way valve 10 was opened to allow the adding of methanol to the reactor tubes 3 of individual channels. The lead valve 23 of the four-way valve 10 was closed. The adjustable-speed motor 7 was turned on and controlled to an appropriate rotation speed to start the washing. The above process was repeated to wash the resin three times. The three-way valve 20 was regulated for communication with the vacuum connection port 19. The lead valve 21 of the three-way valve 20 was opened and the vacuuming was maintained until the resin was completely dried. Finally the peptide resin was collected.

The peptide resins in the reactors tubes 3 of the 48 channels were transferred, cleaved with a cleavage solution, precipitated with diethyl ether, washed and dried to give 48 crude peptides.

The purity of 48 crude peptides was tested and the results were listed below.

| ID | 1 | 2 | 3 | 4 | 5 | 6 | 7 | 8 |
|---|---|---|---|---|---|---|---|---|
| Purity | 91.21% | 88.70% | 90.22% | 89.68% | 91.08% | 87.92% | 88.04% | 90.53% |
| ID | 9 | 10 | 11 | 12 | 13 | 14 | 15 | 16 |
| Purity | 89.61% | 92.01% | 87.30% | 88.67% | 90.12% | 87.44% | 89.61% | 91.55% |
| ID | 17 | 18 | 19 | 20 | 21 | 22 | 23 | 24 |
| Purity | 88.39% | 87.92% | 90.87% | 91.42% | 89.31% | 90.83% | 87.80% | 87.94% |
| ID | 25 | 26 | 27 | 28 | 29 | 30 | 31 | 32 |
| Purity | 88.78% | 88.09% | 89.60% | 91.01% | 90.59% | 87.63% | 89.72% | 91.86% |

-continued

| ID | 33 | 34 | 35 | 36 | 37 | 38 | 39 | 40 |
|---|---|---|---|---|---|---|---|---|
| Purity | 90.64% | 91.87% | 89.64% | 87.91% | 87.48% | 90.58% | 91.10% | 87.89% |
| ID | 41 | 42 | 43 | 44 | 45 | 46 | 47 | 48 |
| Purity | 87.99% | 90.40% | 91.03% | 88.20% | 90.81% | 89.70% | 87.29% | 88.90% |

Example 3

The multi-channel peptide synthesizer in Example 1 was employed to synthesize the same peptide sequence with the simultaneous use of reactor tubes in the 48 channels, and the peptide sequence was shown as VRVALCTAGG. The specific process was described as follows.

(1) Swelling of Resin

The reaction temperature was set to 30° C. and the gas bath-heating thermotank 1 was turned on for heating. Fmoc-Gly-Wang Resins were respectively placed in the reactor tubes 3 of individual channels and the cover was covered. A door of the body of the gas bath-heating thermotank 1 was closed. The lead valve 21 of the three-way valve 20 was closed and the four-way valve 10 was regulated for communication with the methylformamide inlet 11. The lead valve 23 of the four-way valve 10 was opened to allow the addition of methylformamide to the reactor tubes 3 of individual channels. Then the lead valve 23 of the four-way valve 10 was closed and the three-way valve 20 was regulated for communication with the nitrogen connection port 18. The lead valve 21 of the three-way valve 20 was opened and controlled to obtain an appropriate gas flow to swell the resin.

(2) Deprotection of Resin

The lead valve 21 of the three-way valve 20 was closed. The three-way valve 20 was regulated for communication with the vacuum connection port 19. The lead valve 21 of the three-way valve 20 was opened to allow the methylformamide in the reactor tubes 3 of individual channels to be pumped. Then the lead valve 21 of the three-way valve 20 was closed and the four-way valve 10 was regulated for communication with the deprotection solvent inlet 9. The lead valve 23 of the four-way valve 10 was opened to allow the adding of the deprotection solvent to the reactor tubes 3 of individual channels. The lead valve 23 of the four-way valve 10 was closed. The three-way valve 20 was regulated for communication with the nitrogen connection port 18. The lead valve 21 of the three-way valve 20 was opened and controlled to produce an appropriate gas flow to start the deprotection.

(3) Washing of Resin and Feeding

The lead valve 21 of the three-way valve 20 was closed. The three-way valve 20 was regulated for communication with the vacuum connection port 19. The lead valve 21 of the three-way valve 20 was opened to allow the liquid in the reactor tubes 3 of individual channels to be pumped. The lead valve 21 of the three-way valve 20 was closed and the four-way valve 10 was regulated for communication with the methylformamide inlet 11. The lead valve 23 of the four-way valve 10 was opened to allow the addition of methylformamide to the reactor tubes 3 of individual channels. Then the lead valve 23 of the four-way valve 10 was closed. The three-way valve was regulated for communication with the nitrogen connection port 18. The lead valve 21 of the three-way valve 20 was opened and controlled to produce an appropriate gas flow to start the washing. The above process was repeated to wash the resin five times. A top cover of the body of the gas bath-heating thermotank 1 was opened. The cover was opened, and the materials in material storage tanks 14 corresponding to Fmoc-Gly-OH were selected and sequentially added to the reactor tubes 3 of individual channels. The cover was covered and the top cover of the body of the gas bath-heating thermotank 1 was closed. The three-way valve was regulated for communication with the nitrogen connection port 18. The lead valve 21 of the three-way valve 20 was opened and controlled to produce an appropriate gas flow to start the condensation of amino acids.

(4) Washing

The lead valve 21 of the three-way valve 20 was closed and then the three-way valve 20 was regulated for communication with the vacuum connection port 19. The lead valve 21 of the three-way valve 20 was opened to allow the liquid in the reactor tubes 3 of individual channels to be pumped. The lead valve 21 of the three-way valve 20 was closed and the four-way valve was regulated for communication with the methylformamide inlet 11. The lead valve 23 of the four-way valve 10 was opened to allow the addition of methylformamide to the reactor tubes 3 of individual channels. The lead valve 23 of the four-way valve 10 was closed. The three-way valve 20 was regulated for communication with the nitrogen connection port 18. The lead valve 21 of the three-way valve 20 was opened and controlled to produce an appropriate gas flow to start the washing. The above process was repeated to wash the resin three times and steps 2-4 were repeated to sequentially perform condensation with Fmoc-Ala-OH, Fmoc-Thr(tBu)-OH, Fmoc-Cys(Trt)-OH, Fmoc-Leu-OH, Fmoc-Ala-OH, Fmoc-Val-OH, Fmoc-Arg(Pbf)-OH and Fmoc-Val-OH.

(5) Washing and Drying of Peptide Resin

The lead valve 21 of the three-way valve 20 was closed. The three-way valve 20 was regulated for communication with the vacuum connection port 19. The lead valve 21 of the three-way valve 20 was opened to allow the liquid in the reactor tubes 3 of individual channels to be pumped. The lead valve 21 of the three-way valve 20 was closed and the four-way valve was regulated for communication with the methanol inlet 8. The lead valve 23 of the four-way valve 10 was opened to allow the adding of methanol to the reactor tubes 3 of individual channels. The lead valve 23 of the four-way valve 10 was closed. The three-way valve was regulated for communication with the nitrogen connection port 18. The lead valve 21 of the three-way valve 20 was opened and controlled to produce an appropriate gas flow to start the washing. The above process was repeated to wash the resin three times. The three-way valve 20 was regulated for communication with the vacuum connection port 19. The lead valve 21 of the three-way valve 20 was opened and the vacuuming was maintained until the resin was completely dried. Finally the peptide resin was collected.

The peptide resins in the reactor tubes 3 of the 48 channels were transferred, cleaved with a cleavage solution, precipitated with diethyl ether, washed and dried to give 48 crude peptides.

The purity of the 48 crude peptides was tested and the results were listed below.

| ID | 1 | 2 | 3 | 4 | 5 | 6 | 7 | 8 |
|---|---|---|---|---|---|---|---|---|
| Purity | 81.24% | 78.79% | 88.22% | 84.18% | 81.78% | 80.91% | 78.74% | 79.33% |
| ID | 9 | 10 | 11 | 12 | 13 | 14 | 15 | 16 |
| Purity | 79.66% | 82.41% | 87.30% | 83.47% | 82.52% | 85.48% | 87.61% | 81.65% |
| ID | 17 | 18 | 19 | 20 | 21 | 22 | 23 | 24 |
| Purity | 86.37% | 81.56% | 79.83% | 81.44% | 80.91% | 79.13% | 77.80% | 82.24% |
| ID | 25 | 26 | 27 | 28 | 29 | 30 | 31 | 32 |
| Purity | 84.56% | 83.29% | 80.04% | 79.01% | 84.19% | 82.73% | 80.02% | 81.46% |
| ID | 33 | 34 | 35 | 36 | 37 | 38 | 39 | 40 |
| Purity | 78.04% | 81.07% | 83.61% | 81.17% | 85.03% | 80.08% | 81.70% | 82.71% |
| ID | 41 | 42 | 43 | 44 | 45 | 46 | 47 | 48 |
| Purity | 85.09% | 79.31% | 86.03% | 83.20% | 80.91% | 84.77% | 78.59% | 80.18% |

In summary, in the use of the multi-channel peptide synthesizer of the invention, a large number of peptide syntheses can be performed simultaneously under constant reaction temperature, which involves simple operation and high efficiency.

The purity test of the crude products prepared in Example 2 showed an average of 89.65% and a deviation amplitude of 5.26% and the purity test of the crude products prepared in Example 3 showed an average of 83.01% and a deviation amplitude of 12.55%.

By comparing the results respectively obtained in Example 2 and Example 3, it was fully demonstrated that when multiple channels were simultaneously used for peptide synthesis, the reaction mixture should be mixed by rotation driven by the adjustable-speed motor of the invention instead of the nitrogen blowing. Such results may be explained by that in the simultaneous use of multiple channels for peptide synthesis, it was difficult to ensure the complete mixing of reactants in each reactor tube by blowing nitrogen, while the rotation driven by the adjustable-speed motor of the invention can facilitate the thorough mixing of reactants in each reactor tube, allowing for good stability.

Described above are merely embodiments of the invention, which are not intended to limit the scope of the invention. Therefore, the equivalent substitutions or the equivalent variations and modifications made without departing from the spirit of the invention should still fall within the scope defined by the appended claims.

What is claimed is:

1. A multi-channel peptide synthesizer, comprising: a gas bath-heating thermotank; and a storage and feeding device; wherein a rotating shaft is provided in the gas bath-heating thermotank; a plurality of reactor tubes are fixed to the rotating shaft; one end of each reactor tube is connected to a solvent-delivering tube through which respective openings at the end of respective reactor tubes are connected in series; the other end of each reactor tube is connected to a pressure hose through which respective openings at the other end of respective reactor tubes are connected in series; a communicating end of the solvent-delivering tube is provided with a first multi-way valve for supplying liquid; a communicating end of the pressure hose is provided with a second multi-way valve for vacuuming or nitrogen blowing; the rotating shaft is driven by an adjustable-speed motor to rotate to drive the reactor tubes to flip vertically; and the storage and feeding device is configured to store materials and feed materials to the reactor tubes.

2. The synthesizer of claim 1, wherein the solvent-delivering tube extends into the rotating shaft at one end of the rotating shaft and extends along an axis of the rotating shaft to an outside of the gas bath-heating thermotank; the pressure hose extends into the rotating shaft at the other end of the rotating shaft and extends along the axis of the rotating shaft to the outside of the gas bath-heating thermotank; and the reactor tubes rotate to drive the solvent-delivering tube and the pressure hose respectively at two ends of the reactor tubes to rotate.

3. The synthesizer of claim 1, wherein a lead valve is provided at a channel port at which the first multi-way valve is connected with the solvent-delivering tube and at a channel port at which the second multi-way valve is connected with the pressure hose, respectively.

4. The synthesizer of claim 2, wherein the first multi-way valve at the communicating end of the solvent-delivering tube is a four-way valve provided with four channel ports, wherein three of the four channel ports of the four-way valve are respectively a methanol inlet, a deprotection solvent inlet and a methylformamide inlet, and another channel port is connected with the solvent-delivering tube and a lead valve of the four-way valve is provided where the another channel port is located.

5. The synthesizer of claim 3, wherein the first multi-way valve at the communicating end of the solvent-delivering tube is a four-way valve provided with four channel ports, wherein three of the four channel ports of the four-way valve are respectively a methanol inlet, a deprotection solvent inlet and a methylformamide inlet, and another channel port is connected with the solvent-delivering tube and a lead valve of the four-way valve is provided where the another channel port is located.

6. The synthesizer of claim 2, wherein the second multi-way valve at the communicating end of the pressure hose is a three-way valve provided with three channel ports, wherein two of the three channel ports of the three-way valve are respectively a nitrogen connection port and a vacuum connection port, and another channel port is connected with the pressure hose and a lead valve of the three-way valve is provided where the another channel port is located; and the nitrogen connection port is connected to a nitrogen pressure cylinder and the vacuum connection port is connected to a vacuum pump.

7. The synthesizer of claim 3, wherein the second multi-way valve at the communicating end of the pressure hose is a three-way valve provided with three channel ports, wherein two of the three channel ports of the three-way valve are respectively a nitrogen connection port and a vacuum connection port, and another channel port is connected with the pressure hose and a lead valve of the three-way valve is provided where the another channel port is located; and the nitrogen connection port is connected to a nitrogen pressure cylinder and the vacuum connection port is connected to a vacuum pump.

8. The synthesizer of claim 1, wherein each reactor tube comprises a cover, a straight tube and a bottom tube which connect to each other; and a top of the cover and a bottom of the bottom tube are respectively provided with a hose connection port, and a top valve and a bottom valve are respectively provided at the hose connection ports.

9. The synthesizer of claim 8, wherein the cover is a rubber seal cover which is detachably connected with the straight tube; and the straight tube is in threaded connection with the bottom tube.

10. The synthesizer of claim 1, wherein the storage and feeding device comprises a material storage tank and a solvent conduit; one end of the solvent conduit extends into the material storage tank, and the other end of the solvent conduit serves as a discharge port configured to feed materials to the reactor tubes and provided with a feeding valve; and a part of the solvent conduit is coiled in a stretchable hose device.

11. The synthesizer of claim 1, wherein the reactor tubes are arranged in two rows and respectively fixed to two sides of the rotating shaft; the rotating shaft is horizontally arranged with both ends mounted on a tank body of the gas bath-heating thermotank by a rotatable seal joint; the rotating shaft is further provided with a vertical solid support for fixing the pressure hose and the solvent-delivering tube; and the tank body of the gas bath-heating thermotank is provided with a vent fan for adjusting temperature and keeping the temperature constant in the tank body.

12. A method of operating the multi-channel peptide synthesizer of claim 1 for peptide synthesis, comprising:
1) setting a reaction temperature; turning on a heating switch of a tank body of the gas bath-heating thermotank; placing a resin in the reactor tube of a channel and closing the unused channel or channels; covering the reactor tube by a cover; closing a door of the tank body of the gas bath-heating thermotank; closing the lead valve of a three-way valve and regulating a four-way valve for communication with the methylformamide inlet; opening the lead valve of the four-way valve to allow the addition of methylformamide to the reactor tube of the channel; closing the lead valve of the four-way valve; and turning on and controlling the adjustable-speed motor to an appropriate rotation speed to swell the resin;
2) turning off the adjustable-speed motor to keep the reactor tubes in a vertical form; regulating the three-way valve for communication with a vacuum connection port; opening the lead valve of the three-way valve to allow the methylformamide in the reactor tubes of individual channels to be pumped; closing the lead valve of the three-way valve and regulating the four-way valve for communication with the deprotection solvent inlet; opening the lead valve of the four-way valve to allow the adding of the deprotection solvent to the reactor tubes of individual channels; closing the lead valve of the four-way valve; and turning on and controlling the adjustable-speed motor to an appropriate rotation speed to start the deprotection;
3) turning off the adjustable-speed motor to keep the reactor tubes in a vertical form; regulating the three-way valve for communication with the vacuum connection port; opening the lead valve of the three-way valve to allow the liquid in the reactor tubes of individual channels to be pumped; closing the lead valve of the three-way valve and regulating the four-way valve for communication with the methylformamide inlet; opening the lead valve of the four-way valve to allow the addition of methylformamide to the reactor tubes of individual channels; closing the lead valve of the four-way valve; turning on and controlling the adjustable-speed motor to an appropriate rotation speed to start the washing; repeating the above process to wash the resin five times; opening a top cover of the tank body of the gas bath-heating thermotank; opening the cover and selecting the materials in their corresponding material storage tanks and adding the materials sequentially to the reactor tubes of individual channels; covering the cover and closing the top cover of tank body of the gas bath-heating thermotank; turning on and controlling the adjustable-speed motor to an appropriate speed to start the condensation of amino acids;
4) turning off the adjustable-speed motor to keep the reactor tubes in a vertical form; regulating the three-way valve for communication with the vacuum connection port; opening the lead valve of the three-way valve to allow the liquid in the reactor tubes of individual channels to be pumped; closing the lead valve of the three-way valve and regulating the four-way valve for communication with the methylformamide inlet; opening the lead valve of the four-way valve to allow the addition of methylformamide to the reactor tubes of individual channels; closing the lead valve of the four-way valve; turning on and controlling the adjustable-speed motor to an appropriate speed to start the washing; repeating the above process to wash the resin three times; and repeating steps 2-4 until the condensation of all desired amino acids is completed; and
5) turning off the adjustable-speed motor to keep the reactor tubes in a vertical form; regulating the three-way valve for communication with the vacuum connection port; opening the lead valve of the three-way valve to allow the liquid in the reactor tubes of individual channels to be pumped; closing the lead valve of the three-way valve and regulating the four-way valve for communication with the methanol inlet; opening the lead valve of the four-way valve to allow the adding of methanol to the reactor tubes of individual channels; closing the lead valve of the four-way valve; turning on and controlling the adjustable-speed motor to an appropriate speed to start the washing; repeating the above process to wash the resin three times; regulating the three-way valve for communication with the vacuum connection port; opening the lead valve of the three-way valve and maintaining the vacuuming until the resin is completely dried; and collecting the peptide resin.

\* \* \* \* \*